United States Patent
Eckert

(10) Patent No.: US 6,784,308 B2
(45) Date of Patent: Aug. 31, 2004

(54) PROCESS FOR THE PREPARATION OF AROMATIC NITRILES

(75) Inventor: Markus Eckert, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/191,269

(22) Filed: Jul. 8, 2002

(65) Prior Publication Data

US 2003/0018209 A1 Jan. 23, 2003

(30) Foreign Application Priority Data

Jul. 9, 2001 (DE) .......................................... 101 33 274

(51) Int. Cl.[7] .................... C07D 263/34; C07D 213/84; C07D 253/14
(52) U.S. Cl. ....................... 558/343; 544/242; 546/286; 548/236
(58) Field of Search ................................ 558/343, 425; 544/242; 546/286; 548/236

(56) References Cited

U.S. PATENT DOCUMENTS 4,211,721 A * 7/1980 Cotter ........................ 260/465

6,331,628 B1 12/2001 Kondo et al. ............... 544/312

FOREIGN PATENT DOCUMENTS

JP 2001039938 A2 * 2/2001

OTHER PUBLICATIONS

Synlett "Catalytic Cyanation of Aryl Halides with NaCN in the Presence of Crowned Phosphine Complexes of Palladium under Solid–liquid Two–phase Conditions" by Tamon Okano, Asahiro Iwahara, and Jitsuo Kiji (month unavailable) 1998 pp. 243–244.

Tetrahedron Letters 40 (month unavailable) 1999 pp. 8193–8195 "A highly catalytic robust palladium catalyzed cyanation of aryl bromides" by Peter E. Maligres, Marjorie S. Waters, Fred Fleitz and David Askin.

* cited by examiner

Primary Examiner—Joseph K. McKane
Assistant Examiner—Ebenezer Sackey
(74) Attorney, Agent, or Firm—Jill Denesvich; Godfried R. Akorli

(57) ABSTRACT

The invention relates to a process for the preparation of aromatic nitriles form halogenoaromatics or aryl perfluorosulfonates and alkali metal cyanides in the presence of palladium catalysts, zinc, and polyethers.

9 Claims, No Drawings

PROCESS FOR THE PREPARATION OF AROMATIC NITRILES

BACKGROUND OF THE INVENTION

The invention relates to a process for the preparation of aromatic nitriles by reaction of halogenoaromatics or aryl perfluorosulfonates with alkali metal cyanides in the presence of palladium catalysts, polyethers, and zinc.

The palladium-catalyzed substitution of halogens in aromatic compounds by alkali metal cyanides is disclosed, for example, in U.S. Pat. No. 4,211,721 or T. Okano et al., Synleft, 1998, page 243. The processes described there, however, have the disadvantage that both the yields and the low turnover numbers of the catalysts (TON) of at most 170 make industrial realization uneconomical. An improved process was presented by Maligres et al. in Tetrahedron Letters, 40, 1999, page 8193. However, the cyanide source used is expensive zinc cyanide, which is not acceptable for the industrial scale. The need therefore existed to develop a process that makes possible the palladium catalyzed cyanation of halogenoaromatics or aryl perfluorosulfonates using cheap alkali metal cyanides with high turnover numbers and yields.

SUMMARY OF THE INVENTION

There has now been found a process for the preparation of aromatic nitrites of the general formula (I)

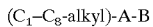   (I)

in which
Ar represents a substituted or unsubstituted aromatic radical, and
n represents one or two,
comprising reacting
(a) an aromatic compound of the general formula (II)

   (II)

in which
Ar and n have the above-mentioned meaning for formula (I), and
X each independently of one another represents chlorine, bromine, iodine, or a perfluoroalkylsulfonyloxy radical,
with
(b) one or more alkali metal cyanides, in the presence of
(c) a palladium catalyst,
(d) zinc, and
(e) one or more polyethers, and
(f) optionally, an aprotic solvent.

DETAILED DESCRIPTION OF THE INVENTION

Substituted or unsubstituted aromatic radicals in this connection mean, for example, carbocyclic aromatic radicals having 6 to 24 ring carbon atoms or heteroaromatic radicals having 5 to 24 ring carbon atoms, in which no ring carbon atom or one, two, or three ring carbon atoms per cycle, but in the whole molecule at least one ring carbon atom, can be substituted by heteroatoms selected from the group consisting of nitrogen, sulfur, and oxygen. Furthermore, the carbocyclic aromatic radicals or heteroaromatic radicals can be substituted by up to five identical or different substituents per cycle, selected from the group consisting of fluorine, nitro, cyano, amino, di($C_1$–$C_6$-alkyl)amino, ($C_1$–$C_6$-alkyl)amino, free formyl or protected formyl, $C_1$–$C_{12}$-alkyl, $C_6$–$C_{12}$-aryl, $C_7$–$C_{13}$-arylalkyl, $C_1$–$C_{12}$-halogenoalkyl, $C_1$–$C_{12}$-halogenoalkoxy, $C_1$–$C_6$-alkylsulfonyl, ($C_6$–$C_{12}$)-arylsulfonyl, ($C_7$–$C_{13}$)-alkylarylsulfonyl, $C_1$–$C_{12}$-acyl, —CO—($C_6$–$C_{12}$)-aryl, $C_1$–$C_{14}$-alkoxycarbonyl, —OCO—($C_6$–$C_{12}$)-aryl, —OCO—($C_7$–$C_{13}$)-arylalkyl, —NHCO—($C_1$–$C_8$)-alkyl, N($C_1$–$C_8$-alkyl)CO—($C_1$–$C_8$)-alkyl, —NHCO—($C_6$–$C_{12}$)-aryl, —NHCO—($C_7$–$C_{13}$)-arylalkyl, —COO—($C_1$–$C_{12}$)-alkyl, —CONH$_2$, —CON($C_1$–$C_6$-alkyl)$_2$, —CONH($C_1$–$C_6$-alkyl), —NCOO—($C_1$–$C_8$)-alkyl, —PO—[($C_1$–$C_8$)-alkyl]$_2$, —PO—[($C_6$–$C_{12}$)-aryl]$_2$, COO—($C_6$–$C_{12}$)-aryl, aryloxy having 6 to 10 ring carbon atoms, heteroaryloxy having 5 to 12 ring carbon atoms of which no ring carbon atom or one, two, or three ring carbon atoms per cycle, but in the whole molecule at least one ring carbon atom, can be substituted by heteroatoms selected from the group consisting of nitrogen, sulfur, and oxygen, or radicals of the general formula (III)

($C_1$–$C_8$-alkyl)-A-B   (III)

in which
A, for example, can represent functionalities selected from the group consisting of

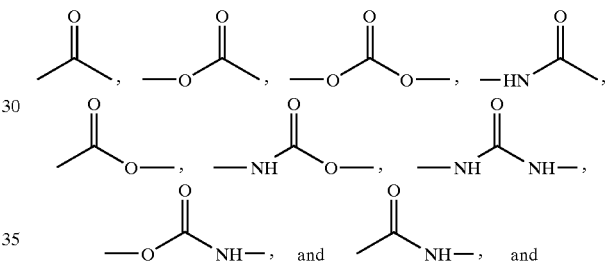

B can represent $C_1$–$C_8$-alkyl, $C_6$–$C_{12}$-aryl, or $C_7$–$C_{13}$-arylalkyl, or A and B together can represent cyano.

Alkyl in the above-mentioned connections, each independently of one another, denotes a straight-chain, cyclic, branched, or unbranched alkyl radical.

Alkoxy in the above-mentioned connections, each independently of one another, denotes a straight-chain, cyclic, branched, or unbranched alkoxy radical.

Halogenoalkyl and halogenoalkoxy in the above-mentioned connections, each independently of one another, denote straight-chain, cyclic, branched, or unbranched alkyl radicals and alkoxy radicals, which can be substituted by one, more than one, or completely by fluorine or chlorine atoms.

Aryl in the above-mentioned connections, each independently of one another, denotes a substituted or unsubstituted aromatic or hetero-aromatic radical.

Examples of carbocyclic aromatic radicals having 6 to 24 ring carbon atoms are, for example, phenyl, naphthyl, biphenyl, binaphthyl, or anthracenyl, and examples of heteroaromatic radicals having 5 to 24 ring carbon atoms in which no ring carbon atom or one, two, or three ring carbon atoms per cycle, but in the whole molecule at least one ring carbon atom, can be substituted by heteroatoms selected from the group consisting of nitrogen, sulfur, and oxygen, are, for example, pyrimidinyl, pyridinyl, oxazolyl, thiophenyl, furanyl, indolyl, triazolyl, or quinolinyl.

For the process according to the invention, aromatic compounds of the general formula (II) are preferably employed, in which Ar represents a substituted or unsubstituted radical from the group consisting of phenyl, naphthyl, binaphthyl, biphenyl, pyrimidinyl, oxazolyl, and pyridinyl, which can be further substituted by no radical or by one, two, or three radicals per cycle, which each independently of one another are selected from the group consisting of fluorine, nitro, cyano, di($C_1$–$C_6$-alkyl)amino, $C_1$–$C_4$-alkyl, $C_6$–$C_{12}$-aryl, $C_1$–$C_{12}$-fluoroalkyl, $C_1$–$C_6$-fluoroalkoxy, $C_1$–$C_4$-acyl, COO—($C_1$–$C_6$)-alkyl, and —CON($C_1$–$C_6$-alkyl)$_2$, n is 1, and X represents chlorine, bromine, iodine, trifluoromethanesulfonyloxy, or onafluorobutanesulfonyloxy.

For the process according to the invention, aromatic compounds of the general formula (II) are particularly preferably employed, in which Ar represents a phenyl radical, which can be further substituted by no radical or by one, two or three radicals, which in each case independently of one another are selected from the group consisting of fluorine, cyano, $C_1$–$C_4$-alkyl, trifluoromethyl, trifluoromethoxy, acetyl, COO—($C_1$–$C_6$)-alkyl, —CON ($C_1$–$C_6$-alkyl)$_2$, n is 1, and X represents chlorine or bromine.

For the process according to the invention, suitable palladium catalysts are, for example, palladium-phosphine complexes that are either prepared in situ from palladium salts and phosphine ligands or are employed as isolated compounds. Preparation in situ from one or more palladium compounds and one or more phosphine ligands is preferred.

Isolated palladium-phosphine complexes that can be employed are, for example, those of the general formula (IV)

$$[PdL_2An_2] \tag{IV}$$

in which

L each represents a monophosphine or $L_2$ together represents a diphosphine, and An represents the anion of an acid.

In the general formula (IV), $L_2$ preferably represents diphosphines of the general formula (V)

$$(R^1)_2P\text{-}A\text{-}P(R^1)_2 \tag{V}$$

in which $R^1$ independently of one another represent straight-chain or cyclic, branched, or unbranched $C_1$–$C_8$-alkyl, phenyl substituted by $R^2$ and $R^3$, naphthyl substituted by $R^2$ and $R^3$, or heteroaryl having 5 to 12 ring carbon atoms and substituted by $R^2$ and $R^3$, where in this radical $R^2$ and $R^3$ each independently of one another represent hydrogen, straight-chain, branched, or cyclic $C_1$–$C_4$-alkyl, straight-chain, branched, or cyclic $C_1$–$C_6$-alkoxy, fluorine, or cyano, A represents an unsubstituted or substituted radical selected from the group consisting of $C_1$–$C_4$-alkylene, 1,2-phenyl, 1,2-cyclohexyl, 1,1'-ferrocenyl, 1,2-ferrocenyl, 2,2'-(1,1'-binaphthyl), and 1,1'-biphenyl, and An represents chloride, bromide, iodide, or acetate.

In the in situ preparation of palladium-phosphine complexes from palladium salts and phosphine ligands, it is possible to employ, for example, monophosphines or diphosphines, diphosphines being preferred.

Preferred diphosphines are those of the general formula (V)

$$(R^1)_2P\text{-}A\text{-}P(R^1)_2 \tag{V}$$

in which $R^1$ and A have the meaning indicated above.

Particularly preferred diphosphines are bis (diphenylphosphino)-propane or 1,1'-bis-diphenylphosphinoferrocene. 1,1'-Bis-diphenylphosphinoferrocene is very particularly preferred.

Palladium compounds employed for the in situ preparation of palladium-phosphine complexes are preferably Pd$_2$(dibenzylideneacetone)$_3$ or those of the general formula (VIa)

$$Pd(Y^1)_2 \tag{VIa}$$

in which $Y^1$ represents chloride, bromide, acetate, methanesulfonate, or trifluoromethane-sulfonate, or palladium compounds of the general formula (VIb)

$$Pd(Y^2)_2L_2 \tag{VIb}$$

in which

Y represents chloride, bromide, acetate, methanesulfonate, trifluoromethane-sulfonate, tetrafluoroborate, or hexafluoro-phosphate, and L each represents acetonitrile, benzonitrile, or benzylnitrile, or $L_2$ together represents 1,5-cyclooctadiene, or palladium compounds of the general formula (VIc)

$$M_2[Pd(Y^3)_4] \tag{VIc}$$

in which $Y^3$ represents chloride or bromide, and

M represents lithium, sodium, potassium, ammonium, or organic ammonium.

Palladium acetate is particularly preferred.

The molar ratio of phosphorus to palladium in the reaction mixture can be, for example, 1 to 10, preferably 1.8 to 2.5.

For the process according to the invention, the molar ratio of halogen or perfluorosulfonate to be replaced to palladium can be, for example, 10 to 10,000, preferably 100 to 2000.

The zinc to be employed according to the invention can be present, for example, in the form of dust, powder, or granules. Use in the form of zinc dust is preferred.

The amount employed can in this case be 1.0 to 100-fold the molar amount of the palladium compound employed, preferably 1.0 to 10-fold.

Polyethers preferably employed in the process according to the invention are those having a molar mass of 100 to 5000 or mixtures of such polyethers. Such polyethers can be, for example, crown ethers such as, for example, 18-crown-6, dibenzo-18-crown-6, and 12-crown-4, cryptands such as, for example, cryptand[2.2.2], branched or unbranched polyethylene glycol ethers such as, for example, glyme, diglyme, or triglyme, or mixtures of polyethylene glycol ethers such as, for example, PEG 200, PEG 300, PEG 400, PEG 600, or PEG 1200. Such mixtures are commercially obtainable, for example, from Merck-Schuchardt and are defined by the average molar mass. PEG 200, PEG 300, and PEG 400 are particularly preferred.

For the process according to the invention, the polyethers can be employed in an amount, for example, from 0.1 ml to 100 ml per liter of reaction mixture. An amount of 1 to 10 g per liter of reaction mixture is preferred. When using polyethers having a molar mass of below 250, such as, for example, glyme or diglyme, they can also function as the sole solvent. In this case, the amount can be chosen, for example, such that per mole of halogenoaromatic or aryl perfluorsulfonate, 50 to 1000 ml (preferably 100 to 500 ml) of polyether are employed.

Alkali metal cyanides that can be employed are, for example, lithium cyanide, sodium cyanide, and potassium cyanide. Sodium cyanide and potassium cyanide are preferred.

For the process according to the invention, for example, 0.95 to 1.5 mol (preferably 1.0 to 1.2 mol) of alkali metal cyanide are employed per halogen or perfluorosulfonate to be replaced.

Optionally, the process according to the invention is carried out in the presence of one or more aprotic solvents. Preferred solvents are cyclic or acyclic ethers such as 1,4-dioxane, tetrahydrofuran, diethyl ether, methyl tert-butyl ether, or di-n-butyl ether, aromatic hydrocarbons such as, for example, toluene, o-xylene, m-xylene, or p-xylene, dipolar aprotic compounds such as, for example, dimethylformamide, N-methylpyrrol-idone, or N-methylcaprolactam, or mixtures of such solvents.

The amount of the aprotic solvent optionally employed can be, for example, 50 ml to 5000 ml (preferably 100 to 500 ml) per mole of the halogenoaromatic or of the aryl perfluorosulfonate employed.

The reaction temperature is, for example, 50 to 170° C., preferably 100 to 140° C.

The reaction can be carried out, for example, at 0.2 to 100 bar. Normal (i.e., ambient) pressure is preferred.

The reaction time can be, for example, 2 h to 72 hours, preferably 12 to 24 hours.

The reaction is preferably carried out under a protective gas atmosphere with extensive exclusion of oxygen and moisture. Suitable protective gases are, for example, nitrogen and rare gases such as, for example, argon, or mixtures of such gases.

In a preferred embodiment, the halogenoaromatic or the aryl perfluorosulfonate is introduced together with the palladium compound, the diphosphine, the zinc, the polyether, and optionally the aprotic solvent, the resultant mixture is stirred at a temperature of 50 to 140° C. for between 3 and 120 minutes to preform the palladium-phosphine complex, and the alkali metal cyanide is then added, if appropriate after intermediate cooling to below 50° C. This procedure has the advantage that deactivation of the palladium compound (for example, by formation of cyanopalladates) is avoided to the greatest possible extent.

The advantage of the process according to the invention lies in the ease with which it can be carried out and the high yields of aromatic nitriles. Furthermore, high catalyst turnover numbers (TON) of over 500 mol of halogenoaromatic/ mol of palladium catalyst are achieved. The process according to the invention is particularly distinguished by the use of the cheap alkali metal cyanides as a cyanide source.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

23.2 g of 3-bromobenzotrifluoride (97% strength), 0.023 g of palladium acetate, 0.11 g of 1,1-bis(diphenylphosphino) ferrocene, and 0.3 g of PEG 400 and also 15 ml of dry toluene were introduced under argon and the mixture was heated to reflux with stirring for 30 minutes. The mixture was cooled (<50° C.), 5.15 g of ground sodium cyanide and 0.078 g of zinc dust were added, and the mixture was heated under reflux for 24 hours with stirring. After cooling, the mixture was filtered and the solution was analyzed by GC (per cent by weight): 10.6 g of 3-trifluoro-methylbenzonitrile were found (62% of theory).

Example 2

As in Example 1, but 26.21 g of 5-bromo-2-chlorobenzotrifluoride (99% strength) were reacted. 19.1 g of 4-chloro-3-trifluoromethylbenzo-nitrile were found (GC analysis: 93% of theory).

Example 3

As Example 1, but the reaction was carried out at 135° C. in 15 ml of degassed xylene with 0.3 g of PEG 200 instead of PEG 400. For work-up, the organic phase was washed three times with water and then fractionally distilled in vacuo. 15.6 g of 3-trifluoromethylbenzonitrile were isolated as a colorless liquid (91% of theory).

Example 4

As Example 2, but 0.082 g of 1,3-bis(diphenylphosphino) propane were employed as a ligand. 18.3 g of 4-chloro-3-trifluoromethylbenzonitrile were found (GC analysis: 89% of theory).

Example 5

As Example 3, but 17.5 g of 4-bromofluorobenzene were reacted. 10.1 g of 4-fluorobenzonitrile were found (GC analysis: 83% of theory.).

Example 6

As Example 2, but 0.012 g of palladium acetate and 0.55 g of 1,1-bis(diphenylphosphino)ferrocene were used. 12.5 g of 4-chloro-3-trifluoro-methylbenzonitrile were found (GC analysis: 61% of theory).

Example 7

26.21 g of 5-bromo-2-chlorobenzotrifluoride (99% strength), 0.046 g of palladium acetate, 0.22 g of 1,1-bis (diphenylphosphino)ferrocene, and 0.3 g of PEG 400 and also 20 ml of dry dioxane were introduced under argon and the mixture was heated to reflux with stirring for 30 minutes. The mixture was cooled to below 50° C. and 15.45 g of ground sodium cyanide and 0.15 g of zinc dust were added, after which the mixture was heated under reflux for 16 hours with stirring. After cooling, the mixture was filtered and the solution was analyzed by GC (per cent by weight): 16.9 g of 4-cyano-3-trifluoromethylbenzonitrile were found (86% of theory).

Example 8

As Example 3, but 24.9 g of 3,5-(bistrifluoromethyl) chlorobenzene were reacted. 15.5 g of 3,5-(bistrifluoromethyl)benzonitrile were isolated as a colorless liquid (65% of theory).

What is claimed is:

1. A process for the preparation of aromatic nitriles of the formula (I)

    (I)

In which
Ar represents a substituted or unsubstituted aromatic radical, and
n represents one or two,
comprising reacting
(a) an aromatic compound of the formula (II),

    (II)

In which
Ar and n have the above-mentioned meaning for formula (I), and
X each independently of one another represents chlorine, bromine, iodine or a perfluoroalkylsulfonyloxy radical with
(b) one or more alkali metal cyanides,
in the presence of
(c) a palladium catalyst and
(d) zinc and
(e) one or more polyethers.

2. A process according to claim 1 further including adding an aprotic solvent.

3. A process according to claim 1 wherein, in the aromatic compound of the formula (II), Ar represents a substituted or unsubstituted radical from the group consisting of phenyl, naphthyl, binaphthyl, biphenyl, pyrimidinyl, oxazolyl, and pyridinyl, which can be further substituted by no radical or one, two, or three radicals, which each independently of one another are selected from the group consisting of fluorine, nitro, cyano, di($C_1$–$C_6$-alkyl)amino, $C_1$–$C_4$-alkyl, $C_6$–$C_{12}$-aryl, $C_1$–$C_{12}$-fluoralkyl, $C_1$–$C_6$-fluoralkoxy, $C_1$–$C_4$-acyl, COO—($C_1$–$C_6$)-alkyl, and —CON($C_1$–$C_6$-alkyl)$_2$, n is 1, and X represents chlorine, bromine, iodine, trifluoromethanesulfonyloxy, or nonafluorobutane-sulfonyloxy.

4. A process according to claim 1 wherein the palladium catalyst is generated in situ from a palladium compound and a phosphine ligand.

5. A process according to claim 4 wherein the phosphine ligand is a diphosphine.

6. A process according to claim 4 wherein the addition of the alkali metal cyanide takes place after the preformation of the palladium-phosphine complex.

7. A process according to claim 1 wherein the polyethers have a molar mass of 100 to 5000.

8. A process according to claim 1 wherein the alkali metal cyanide is sodium cyanide or potassium cyanide.

9. A process according to claim 1 carried out at a temperature of 50 to 170° C.

* * * * *